United States Patent [19]

Payne et al.

[11] Patent Number: 5,099,693
[45] Date of Patent: Mar. 31, 1992

[54] APPARATUS FOR INVESTIGATING A SAMPLE WITH ULTRASOUND

[75] Inventors: Peter A. Payne; Richard J. Dewhurst, both of Manchester, England

[73] Assignee: Cogent Limited, London, England

[21] Appl. No.: 597,092

[22] Filed: Oct. 15, 1990

Related U.S. Application Data

[63] Continuation of Ser. No. 456,588, Jan. 2, 1990, abandoned, which is a continuation of Ser. No. 276,174, Nov. 25, 1988, abandoned.

[30] Foreign Application Priority Data

Nov. 27, 1987 [GB] United Kingdom ............ 8727875

[51] Int. Cl.$^5$ .......................................... G01N 29/00
[52] U.S. Cl. ........................................ 73/632; 73/643
[58] Field of Search ............. 73/632, 643, 655, 629; 310/336, 371

[56] References Cited

U.S. PATENT DOCUMENTS

| | | | |
|---|---|---|---|
| 4,137,991 | 2/1979 | Melcher et al. | 181/142 |
| 4,379,409 | 4/1983 | Primbsch et al. | 73/643 |
| 4,683,750 | 8/1987 | Kino et al. | 73/643 |

OTHER PUBLICATIONS

"Laser Generation of Directional SAW Pulses in Metals", by Aindow et al., Optics Communications, vol. 42, No. 2, Jun. 1982.
Aindow, A. M. et al., *The Efficient Production of Acoustic Pulses at Free Metal Surfaces by Q-Switched Lasers*, Proc. of the 4th Nat. Quant. Electronics Conf., 19-21 Sep. 1979, pp. 255-258.
Hutchins, D. A. et al., *Laser Generation of Longitudinal and Shear Pulses in Metals*, Proc. of the Inst. of Acoustics, 8-11 Apr., 1980, pp. 281-285.
Aindow, A. M. et al., *The Laser-Generation of Surface Elastic Waves at Free Metal Surfaces*, Porc. of the Inst. of Acoustics, 8-11, Apr. 1980, pp. 277-280.
Scruby, C. B. et al., *Quantitative Studies of Thermally-Generated Elastic Waves in Laser-Irradiated Metals*, J. Appl. Phys., 51, pp. 6210-6216, 1980.
Aindow, A. M. et al., *Characteristics of a Laser-Generated Acoustic Source in Metals*, Proc. of 1980 Euro. Conf. on Optical Systems and Applications, SPIE, vol. 236, pp. 478-485, 1980.
Aindow, A. M. et al., *Laser-Generated Ultrasonic Pulses at Free Metal Surfaces*, J. Acoust. Soc. Amer., 69, pp. 449-455, 1981.
Scruby, C. B. et al., *A Laser-Generated Standard Acoustic Emission Source*, Materials Evaluation, 39, pp. 1250-1254, 1981.
Hutchins D. A. et al., *Estimation of Liquid Depth by Laser Generation of Ultrasound*, Acoustic Letters, 4, pp. 96-99, 1980.
Hutchins, D. A. et al., *Laser Generation as a Standard Acoustic Source in Metals*, Appl. Phys. Lett., 38, pp. 677-679, 1981.
Hutchins, D. A. et al., *Mechanisms of Laser-Generated Ultrasound by Directivity Pattern Measurements*, Proc. of Ultrasonics, 1981, 30 Jun.-2 Jul., pp. 20-25.
Scruby, C. B. et al., *Quantitative Studies of Laser-Generated Acoustic Waveforms*, Proc. of Ultrasonics, 1981, 30 Jun.-2 Jul., pp. 129-134.
Dewhurst, R. J. et al., *Quantitative Measurements of Laser-Generated Acoustic Waveforms*, J. Appl. Phys., 53, pp. 4064-4071, 1982.
Hutchins, D. A. et al., *Some Applications of Laser-Generated Ultrasound in Metals*, Proc. IEEE, 1981, Ultrasonic Symposium, pp. 798-801.

(List continued on next page.)

*Primary Examiner*—Hezron E. Williams
*Assistant Examiner*—Louis M. Arana
*Attorney, Agent, or Firm*—Wolf, Greenfield & Sacks

[57] ABSTRACT

An apparatus for investigating a sample with ultrasound has a probe head formed by a casing, a transducer element of piezoelectric plastics material, and a source for applying a high frequency pulse to the sample. The source is preferably one end of an optical fibre, which fibre extends to a laser remote from the probe head. The transducer element is connected to the sample by an acoustic coupling medium, e.g. water. Thus, the probe head can be moved relative to the sample, and a compact, but efficient, structure is achieved.

7 Claims, 2 Drawing Sheets

OTHER PUBLICATIONS

Hutchins, D. A. et al., *Directivity Patterns of Laser-Generated Ultrasound in Aluminum*, J. Acoustic, Soc. Amer., 70, pp. 1362–1369, 1982.

Aindow, A. M. et al., *Laser-Generation of Directional Surface Acoustic Wave Pulses in Metals*, Opt. Comm., 42, pp. 116–120, 1982.

Scruby, C. B. et al., *Laser-Generation of Ultrasound in Metals*, Research Techniques in Non–Destructive Testing, vol. v, Chp. 8, pp. 284–327, Academic Press, 1982.

Aindow, A. M. et al., *The Physics of Laser-Generated Surface Acoustic Waves in Metals*, Quantum Elevtronics and Electro-Optics, ed. P. L. Knight, John Wiley, pp. 427–430, 1983.

Dewhurst, R. J. et al., *The Performance of Thick Piezoelectric Transducers as Wideband Ultrasonic Detectors*, Ultrasonics, 21, pp. 79–84, 1984.

Aindow, A. M. et al., *Crack Depth Estimation Using Wideband Laser Generated Surface Acoustic Waves*, Proc. of Ultrasonics International '83, (Halifax, Canada), pp. 20–24.

Dewhurst, R. J., *A Hand-Held Laser-Generator of Ultrasonic Pulses*, Non-Destructive Testing Communications, 1, pp. 93–104, 1983.

Aindow, A. M. et al., *Laser-Based Non-Destructive Testing Techniques for the Ultrasonic Characterisation of Sub-Surface Flaws*, NDT International, 17, pp. 329–335, 1984.

Cooper, J. A. et al., *The Application of Laser-Generated Ultrasound to the Remote Testing of Laminar Defects*, Proc. of Ultrasonics International '85 (Brighton, UK), pp. 207–212.

Crosbie, R. A. et al., *Flexural Resonance Measurements of Clamped and Partially Clamped Discs, Excited by Nanosecond Laser Pulses*, J. Appl. Phys. 59, pp. 1843–1848, 1986.

Cooper, J. A. et al., *Characterisation of Surface Breaking Defects in Metals Using Laser-Generated Ultrasound*, Phil. Trans. Roy. Soc. London, Series A, 320, pp. 319–328, 1986.

Cooper, J. A. et al., *Surface Acoustic Wave Interactions With Cracks and Slots: A Noncontacting Study Using Lasers*, IEEE Trans. in Ultrasonics, Ferroelectrics and Frequency Control, UFFC-33, pp. 462–470, 1986.

Dewhurst, R. J. et al., *Further Evidence for Two-Component Surface Acoustic Wave Reflections from Surface--Breaking Slots*, Appl. Phys. Lett., 49, pp. 1694–1695, 1986.

Dewhurst, R. J. et al., *Non-Contact Detection of Surface-Breaking Cracks Using a Laser Acoustic Source and An Electromagnetic Acoustic Receiver*, Appl. Phys. Lett., 49, pp. 374–376, 1986.

APPARATUS FOR INVESTIGATING A SAMPLE WITH ULTRASOUND

This application is a continuation of application Ser. No. 07/456,588, filed Jan. 2, 1990, now abandoned, which is a continuation of application Ser. No. 276,174, filed Nov. 25, 1988, now abandoned.

The present invention relates to an apparatus for investigating a sample with ultrasound.

It is known that an ultrasonic signal may be generated in a material by causing a high frequency pulse of radiation from e.g. a laser to be incident on the surface of that material. It is also known to use a laser to detect the behaviour of ultrasonic waves within a material, thereby to detect variations in the material due to e.g. the presence of different layers, defects, etc.

In general, such known systems use a system of mirrors, lenses, etc., to focus the laser radiation on the material, but this greatly limits the configuration of an ultrasonic probe, because the size of the laser, and the optical components, limit the optical path that may be used. Nevertheless, a short duration laser pulse is capable of generating ultrasound with very high frequency components in a sample, in contrast to standard ceramic piezoelectric transducers which do not generate such high frequency ultrasound so well.

In the present invention, radiation from e.g. a laser is guided to the surface of the sample. This generates ultrasound, which is detected by a piezoelectric transducer comprising a piezoelectric transducer element, acoustically connected to the surface e.g. by a suitable transmission medium.

It has been thought that it was necessary to separate physically the optical fibre and the transducer, to prevent the radiation in the fibre affecting the transducer. It was feared that this problem would be most acute if a piezoelectric plastics material was used to form the transducer element. If heating of the piezoelectric material occurred, it would be vapourised. If the piezoelectric plastics material was PVDF, this would release fluorine compounds, leading to a health hazard. However, it has been found that the optical fibre wholly constrains the radiation so that the piezoelectric material is unaffected. Hence it has been realised that it is possible to us piezoelectric plastics materials, which have superior properties for detection of high frequency signals (because it is possible to make the transducer element as a very thin film).

According to the present invention, the piezoelectric transducer is of piezoelectric plastics material, and the piezoelectric transducer and the source (from which issues the radiation pulse) are contained in a casing, thereby forming an integral probe head. Preferably, the source is formed by one end of an optical fibre. The fibre extends from that end out of the casing to a radiation generator such as a laser. Alternatively, a small semiconductor laser may be provided in the casing. The rest of the probe may include e.g. the laser for generating the radiation pulses, which laser is coupled to the fibre, and electronic processing circuitry for processing the signals generated by the piezoelectric transducer.

The exact geometry of the transducer element and fibre end within the casing are not critical to the present invention. The fibre may extend to a point proximate the sample, to achieve concentration of the laser radiation. Alternatively, however, the end of the fibre can be further away from the sample surface, so that a larger area of sample is affected. The angle of divergence of the laser beam is normally about 15° from a standard fibre. However, it is also possible to modify this angle by providing one or more optical elements at the end of the fibre, as will be discussed in more detail later.

The fibre may pass around the transducer element within the casing. However, it is quite possible (and preferred) for the optical fibre to extend through the transducer element, so that the transducer element is directly over the point of incidence of the radiation, with the direction of incidence being substantially normal to the surface. Alternatively, particularly when the optical fibre passes around the transducer element, the angle of incidence of the radiation may be inclined to the surface.

Preferably, the transducer includes an arrangement for causing it to have an effective focus at or adjacent the surface corresponding to the point of incidence of the radiation from the optical fibre, or to a point within the sample which is under investigation. In general, it is easiest if this focusing is achieved geometrically, e.g., by suitable shaping of the transducer element. Using a piezoelectric polymer material, this is relatively easy. However, it is also possible to use electronic focusing by providing a transducer element in the form of a phased array. In this arrangement, a plurality of active transducer regions (e.g. concentric annuli) may be provided, and the analysis circuitry connected to that transducer be arranged to detect signals at each active region, with an adjustable delay between the times of detection at those active regions. The delay times, when suitably adjusted, effectively give the array a focus, since only radiation from a particular point will reach the active regions with delays between them corresponding to the delays set by the analysis circuitry. The advantage of this system is that adjustment of the delay time permits the focus of the phased array to be varied e.g. to different depths in the sample.

Where the transducer element is focussed (however that is achieved) it is desirable that the point of incidence of the beam on the sample is coincident, or at least coaxial, with the transducer focus. In some cases it is preferable if the transducer focus is located within the sample, rather than at its surface, as this improves the study of features within the sample.

In general, the main interest in the material is not simply in the surface, but in the structure below that surface. Thus, for example, it may be of interest to analyse a multi-layer structure, or to detect defects, etc., in the material. Diffraction at the interface between the material to be studied and the coupling medium between that material and the transducer will cause the wave to pas through the acoustic medium to the transducer.

As was mentioned above, the pulse of radiation from the laser needs to be of short time duration leading to an acoustic wave containing high frequency components. This is particularly important because the higher frequency waves provide better resolution of features to be examined in the material. An upper limit for the duration of the pulse is 200 ns with a preferred upper limit of 100 ns. Typically, the pulse will have a duration of 20 ns. Since, the frequency response of the transducer is needed to detect high frequency signals. Normally, a thickness of 25μ or less is needed. The use of a piezoelectric polymer to form the transducer element satisfies this requirement, because piezoelectric polymer films may be made very thin. This is particularly useful if an ultrasonic probe incorporating the present invention is used in a scanning acoustic microscope. At present, such microscopes are limited in use to very thin samples, e.g. tens of microns thick, but the use of an ultrasonic prove head incorporating the present invention, with a high frequency laser pulse and a thin piezoelectric polymer transducer element, enables thicker samples to be investigated. This is particularly important when the sample is a biological material.

An ultrasonic probe head incorporating the present invention may be hand-mounted on a surface, to enable a simple test to be done, or a suitable mechanical system may permit the probe to scan across a surface. This latter is particularly useful in non destructive testing of materials, such as films, etc., and may also find application in the study of semiconductor wafers or ceramics.

Embodiments of the invention will now be described, by way of example, and with reference to the accompanying drawings in which:

DETAILED DESCRIPTION OF THE PREFERRED EMBODIMENTS

Figure 1:
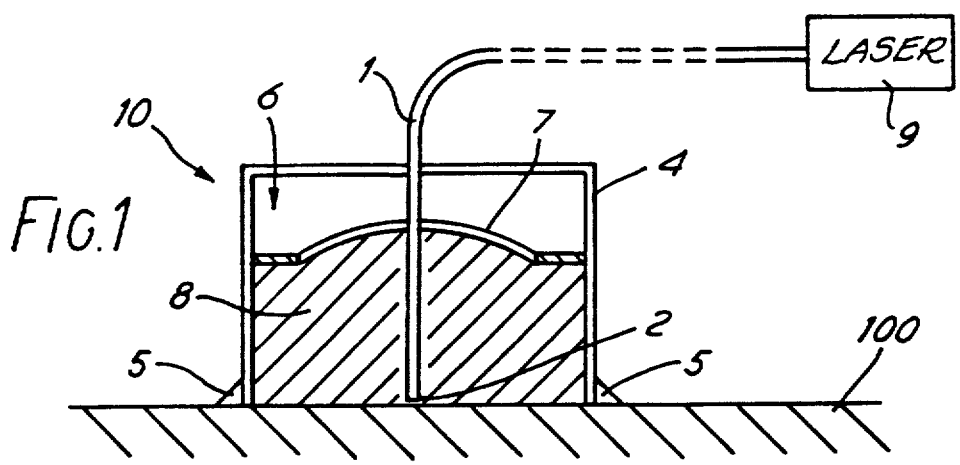
FIG. 1 shows a first embodiment of the present invention.

The first embodiment shown in FIG. 1 provides an apparatus having a cylindrical casing 4, open at one end. The casing 4 lies on the surface of the sample 100 which is to be tested with open end of the casing 4 in contact with the sample 100. A seal 5 may be provided at the rim of the open end of the casing 4 for good contact between the surface of the sample and the casing 4.

The casing 4 contains a transducer 6 which has a piezoelectric transducer element 7 formed as a substantially spherical dish, whose focus lies at a point on the surface of the sample 100. The rest of the transducer 6 will normally include a backing material for supporting the transducer element 7. The transducer element 7 is made of a piezoelectric polymer (e.g. PVDF) which permits it to be shaped in the desired way and also enables the transducer element to be made thin, to enable it to respond to high frequency ultrasound. A typical thickness would be around 1 82 m for ps or ns pulses of radiation from the laser. An optical fibre 1 is passed through the pole of the element 7 so that the free end 2 of the fibre 1 may lie substantially perpendicular to the plane of the surface of the sample 100. As illustrated in FIG. 1, the free end 2 of the fibre 1 is proximate the surface of the sample, but this is not essential as will be discussed later.

The volume of the casing 4 between the element 7 and the surface of the sample 1 is filled with an acoustic coupling medium 8. The coupling medium 8 should be chosen so that it does not affect the sample 100 in any way, and should also have good acoustic transmission properties. Liquids are normally used, and a typical coupling medium is water which is retained in he casing by virtue of the contact the seal 5 makes with the surface of the sample 100. It is also possible, however, to use a gel medium (transparent to ultrasound) or possibly a suitable solid.

The end of the optical fibre 1 remote from the free end 2 is connected to a laser 9, e.g. a laser known as a Type IV laser, which produces radiation pulses having short pulse duration e.g. less than 200 ns. The pulse length is preferably less than 100 ns and a typical pulse may be 20 ns. This gives the pulse a centre frequency of approximately 50 MHz. The energy of the pulse is typically in the range of 10 $\mu$J to 1 mJ but energies outside this range may be used if desired. The diameter of the fibre 1 should be sufficiently large to provide good transmission of laser radiation, but is limited by the need for the fibre to be sufficiently flexible. Fibre diameters of approximately 0.6 mm to 1 mm have been found to be satisfactory; this is also the case for other embodiments to be described later. Thus, for example, the fibre 1 can be a 600 $\mu$optical core with a standard outer cladding. Thus, the casing 4, the transducer 6 and the end of the fibre 1 form a probe head 10 which, due to the flexibility of the fibre 10, may be moved relative to the laser 9. When the laser is switched on, radiation pulses are transmitted down the optical fibre 1, and thereby set-up ultrasonic frequency vibrations in the sample, i.e. ultrasound. The ultrasound propagates through the sample 100 and some is reflected back toward the probe 10, progagates through the acoustic coupling medium 8, and causes the PVDF transducer 6 to generate electrical signals which are fed to a signal processing system (not shown). In some cases, it is possible that the strongest electronic signals are produced by the transducer 6 if the focus of the transducer element 7, and the point at which the laser radiation from the optical fibre passes into the sample 100, are coincident. Thus it may be said that the probe is geometrically "focused" to receive the strongest signals. In other applications the focus of the spherical transducer element will not be coincident with the point at which the laser radiation from the optical fibre passes into the sample 100, but instead will focus to some point within the sample, whose depth lies in an area of interest, for example a depth where debonded defects may be present.

Typically the transducer element 7 will be positioned between 5 mm and 50 mm from the surface of the sample 100.

For some purposes, the probe may be mounted on the sample 100 by hand. However, for industrial purposes it may be necessary to move the probe on the surface using e.g. a robot arm. Furthermore, where the sample 100 is produced as part of a continuous process, it may itself move below a fixed, or reciprocating, probe.

In this embodiment the optical fibre 1 extends through element 7, to a point proximate the sample surface. Alternatively, the fibre 1 may terminate close to the element 7. In this latter case the optical fibre end may be modified with additional optical elements which create laser beams with differing spatial intensity cross-sections. For example, a convex microlens may be placed at the end 2 of the optical fibre 1 so that the laser beam is focussed to a spot on the surface of the sample 100. In one form of the probe head 10 this spot will be coincident with the focus of the transducer element 7. In another example, the microlens may be concave, so that the laser beam diverges strongly from the end 2 of the optical fibre 1 to the surface of the sample 100. This creates ultrasound which is essentially a plane wave incident on the sample 100 in a direction normal to the surface of the sample 100.

Figure 2:
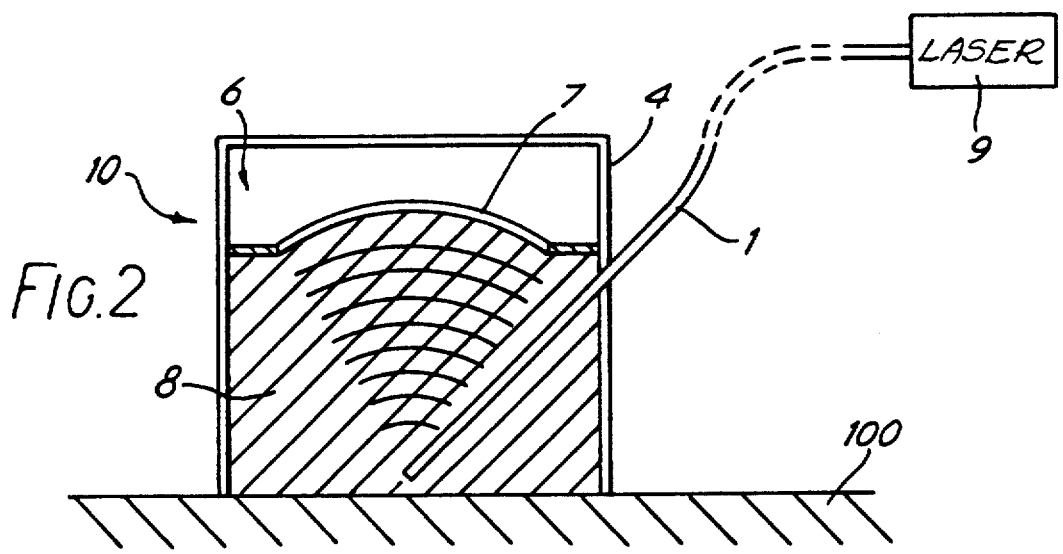
FIG. 2 shows a second embodiment of the present invention.

In a second embodiment of the present invention, shown in FIG. 2, the optical fibre 1 is passed through the side of the casing 4.

This embodiment is easier and cheaper to construct, as the optical fibre does not pass through the transducer element 7. Other parts of the probe head 10 are the same as the first embodiment shown in FIG. 1, and the same reference numerals are used for corresponding features.

Figure 3:
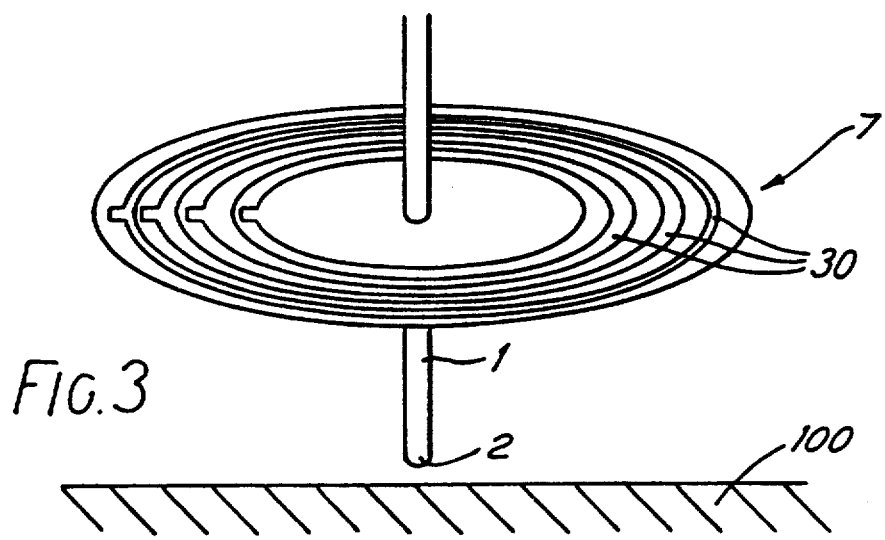
FIG. 3 shows a third embodiment of the present invention.

In a third embodiment focusing of the probe head is achieved not by a geometrical method but electronically using a phased array element. FIG. 3 shows a perspective view of part of a probe head whose casing, acoustic coupling medium, seals (none of which are shown for the sake of convenience) and dimensions may be similar to those described above for the first two embodiments.

The piezoelectric element 7 of the transducer 6 (the remainder of which is not shown) is plane and circular in shape and has concentric annuli 30 of active piezoelectric regions. This configuration is known as a phased array and each of these annuli 30 is connected to suitable processing circuitry (not shown). The circuitry is usually activated when the laser pulse is fired, and detects the ultrasound signal in a given annulus after a given time interval. The time interval between one annulus and the next is calculated so that it is equal to the difference in time required for soundwaves to travel path lengths corresponding to the distances of those annuli from a selected point in the sample 100, which point becomes the focus of the element 7. This arrangement has the advantage that the time intervals between the annuli can be changed, and thus the transducer may be set for different path lengths corresponding to different depths of focus in the sample 100. This means that a single position of the probe head can test more areas of the sample, and thus testing may be achieved in a shorter time.

A further embodiment, illustrated in FIG. 4, will now be described, which is the currently preferred embodiment of the present invention.

In general, parts of this embodiment correspond to parts of the first embodiment, shown in FIG. 1 and corresponding reference numerals are used. Thus, the piezoelectric transducer 6 is contained within a casing 4, and an optical fibre 1 extends into that casing from a laser 9. Thus, once again, a probe head 10 is formed by the transducer element 6, the casing 4 and the free end of the optical fibre 1.

Figure 4:
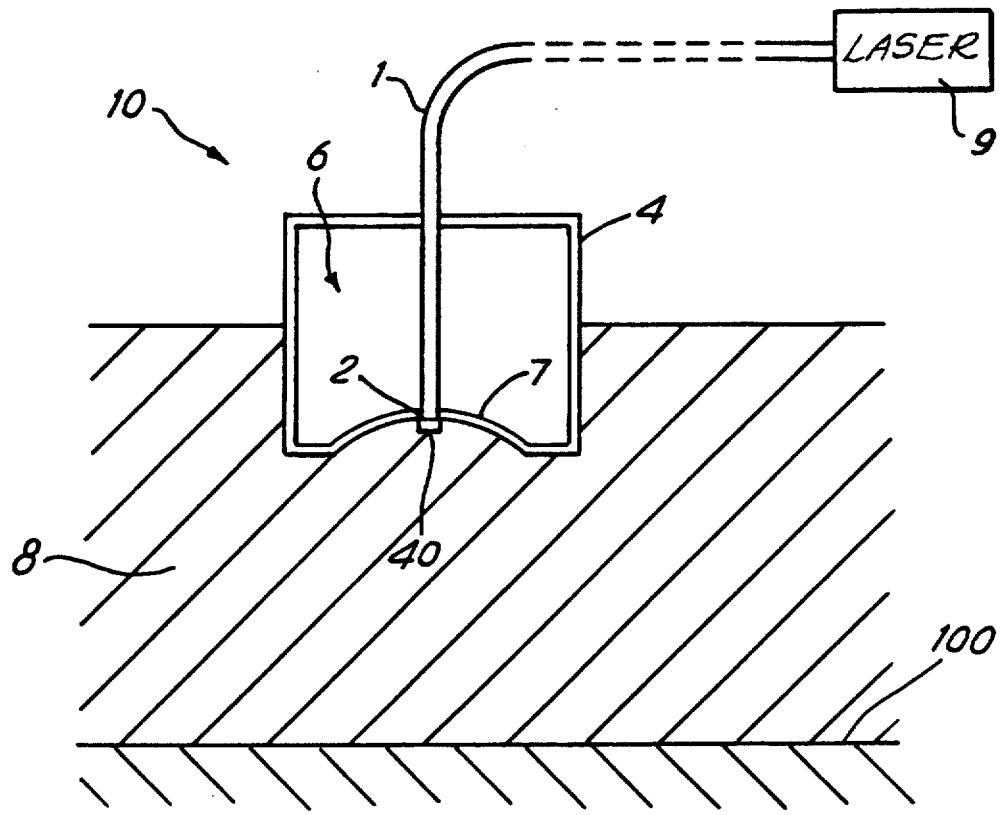
FIG. 4 shows a fourth embodiment of the present invention.

However, in the embodiment shown in FIG. 4, the transducer element 7 of the transducer 6 is coupled to the surface of the sample 100 by an acoustic coupling medium 8 which is not constrained within the casing 4. Instead, the acoustic coupling medium 6 (which is preferably a liquid) forms a bath above the surface, with the probe heat 10 extending at least partially into that medium 8. For this reason, the casing 4 does not extend beyond the transducer element 7 towards the surface 100, and in this embodiment the free end 2 of the optical fibre 1 terminates close to the transducer element 7, rather than close to the surface 100.

Again, as illustrated in FIG. 4, the focussing of the transducer element is achieved by shaping it, but it is also possible to use the electronic focusing system of FIG. 3.

FIG. 4 illustrates a further feature of the present invention, discussed above, in that an optical element 40 is provided at the free end 2 of the optical fibre 1. This optical element 40 may be a lens to converge (or diverge) the laser beam pulse onto the surface 100. Thus, the desired intensity of beam, and the desired area of surface to be effected can be selected. The size of the "spot" of the laser beam incident on the surface is not critical to the invention. Spots less than 10 $\mu$m are possible, but unusual, since if the spot is very small, the intensity of the radiation within that spot could cause damage to the surface of the sample 100. A further possibility is that an array of slits may be provided at the end of the fibre, so that interferences effects produce quasi-single frequency ultrasound, rather than a range of frequencies about a central frequency, as would be normal in a pulse.

Although the present invention has been discussed above using a single optical fibre, it is also possible to use a bundle of fibres to guide the radiation from the laser to the sample.

Figure 5:
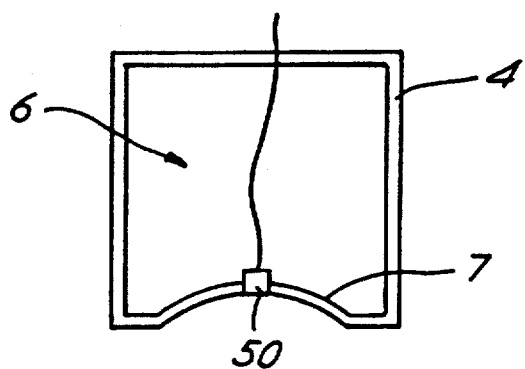
FIG. 5 a fifth embodiment of the present invention.

In all the embodiments discussed above, the optical pulse has been guided by an optical fibre delivery system. However, it may be possible to use a laser diode or similar semiconductor laser positioned in the casing. Such a device would have to be extremely small to prevent it blocking ultrasound from the surface. An embodiment of this is shown in FIG. 5, with the laser diode being shown at 50, and parts corresponding to those of the other embodiments being indicated by the same reference numerals as before. The problem here is to form the opening in the piezoelectric element 7 to receive the laser diode 50, and it would be essential that the piezoelectric element 7 is suitably supported by a backing material of the transducer 6. In practice, it is more likely that, even when a semiconductor diode is used, an optical fibre will be used to guide the radiation from it through the piezoelectric element 7.

What is claimed is:

1. An apparatus for investigating a sample with ultrasound, comprising:
   an optical radiation source for producing a high frequency pulse of said optical radiation;
   optical fibre means for transmitting said optical radiation from said source to said sample with said transmitted radiation emanating from a first end of said optical fibre means;
   a transducer element of a piezoelectric plastics material for detecting ultrasound generated by said pulse in the sample, said transducer element being shaped to have a focus at a point corresponding to the incidence of the radiation on the sample from said first end of said optical fibre means;
   a casing containing said transducer element and said first end; and
   an acoustic coupling medium for coupling said transducer element to said sample.

2. An apparatus according to claim 1, wherein said source comprises a laser to which said optical fibre means extends.

3. An apparatus according to claim 2, wherein said laser is remote from said optical fibre first end.

4. An apparatus according to claim 1, wherein said source is a semiconductor laser.

5. An apparatus according to claim 1, wherein said source first end is located within said acoustic coupling medium.

6. An apparatus according to claim 5, wherein said optical fibre means extends from said first end in the acoustic coupling medium, through said transducer element to a point remote from said sample.

7. An apparatus according to claim 1, further comprising a microlens between said first end and said sample, said microlens being for modifying the divergence of the radiation from said first end.

* * * * *

UNITED STATES PATENT AND TRADEMARK OFFICE
CERTIFICATE OF CORRECTION

PATENT NO. : 5,099,693

DATED : March 31, 1992

INVENTOR(S) : Peter A. Payne, et al.

It is certified that error appears in the above-indentified patent and that said Letters Patent is hereby corrected as shown below:

Column 1, line 46, "us" should be "use".

Column 2, line 53, "pas" should be "pass".

Column 3, line 14, "non destructive" should be "non-destructive".

Column 3, line 53, "1 82m" should be "1 $\mu$m".

Column 4, line 18, "$\mu$optical" should be "$\mu$m optical".

Column 6, claim 5, line 58, delete "source".

Signed and Sealed this

Fourteenth Day of March, 1995

Attest:

BRUCE LEHMAN

Attesting Officer

Commissioner of Patents and Trademarks